US012653571B2

(12) United States Patent
    Hammerling

(10) Patent No.: US 12,653,571 B2
(45) Date of Patent: Jun. 16, 2026

(54) TAP BLOCK INJECTION DEVICE

(71) Applicant: ProMedica Health System, Inc.,
     Toledo, OH (US)

(72) Inventor: Jay Hammerling, Ottawa Hills, OH
     (US)

( * ) Notice: Subject to any disclaimer, the term of this
     patent is extended or adjusted under 35
     U.S.C. 154(b) by 982 days.

(21) Appl. No.: 17/805,942

(22) Filed: Jun. 8, 2022

(65) Prior Publication Data

US 2022/0387302 A1      Dec. 8, 2022

Related U.S. Application Data

(60) Provisional application No. 63/208,293, filed on Jun.
     8, 2021.

(51) Int. Cl.
     *A61B 17/34*      (2006.01)
     *A61B 17/00*      (2006.01)
     *A61J 1/20*       (2006.01)
     *A61K 9/00*       (2006.01)
     *A61M 5/142*      (2006.01)
     *A61M 25/06*      (2006.01)

(52) U.S. Cl.
     CPC ......... *A61B 17/3401* (2013.01); *A61J 1/2093*
            (2013.01); *A61K 9/0019* (2013.01); *A61B*
            *2017/00867* (2013.01); *A61M 2005/14284*
            (2013.01); *A61M 2025/0681* (2013.01); *A61M*
            *2205/276* (2013.01)

(58) Field of Classification Search
     CPC ................ A61K 9/0019; A61J 1/2093; A61B
            2017/00867; A61B 17/3478; A61B
            17/3496; A61B 17/3401; A61M 2005/14284; A61M 2205/276; A61M
     2205/3317; A61M 5/46; A61M 2205/582;
     A61M 5/321; A61M 2005/1585; A61M
     2205/0266; A61M 2210/1021; A61M
     5/158; A61M 25/0133; A61M 25/0136;
     A61M 2025/0681
     See application file for complete search history.

(56) References Cited

U.S. PATENT DOCUMENTS 4,834,722 A * 5/1989 Zenz ..................... A61M 5/158
                                                   604/533
     5,019,049 A * 5/1991 Haining ............ A61M 25/0631
                                                   604/165.02
     5,152,749 A * 10/1992 Giesy ................. A61B 17/3415
                                                   604/533

(Continued)

*Primary Examiner* — James D Ponton

(57)                ABSTRACT

A device for performing a transversus abdominis plane
(TAP) block anesthetic injection during a laparoscopic sur-
gical procedure. The device includes a handle, a needle fixed
to the handle, and a sheath covering the needle. The sheath
is slidably retractable via a thumb-operated slider on the
handle. In a first position for device insertion, the sheath
fully covers the tip of the needle, preventing the needle from
puncturing any organ or tissue in the patient. In a second
position, the sheath is retracted using the slider to expose the
needle tip, enabling insertion of the needle tip into the
appropriate tissue and injection of the anesthetic. The needle
and sheath have a length suitable for reaching the desired
abdominal location from outside the body through the
laparoscopic port. A threaded luer and tube, fluidly coupled
to the needle, are used to push the anesthetic through the
needle and into the tissue.

18 Claims, 7 Drawing Sheets

(56)  References Cited

U.S. PATENT DOCUMENTS

| | | | |
|---|---|---|---|
| 5,817,074 A * | 10/1998 | Racz | A61M 19/00 |
| | | | 604/272 |
| 6,238,389 B1 | 5/2001 | Paddock et al. | |
| 2010/0114017 A1 | 5/2010 | Lenker et al. | |
| 2012/0023238 A1 | 1/2012 | Bouthemy et al. | |
| 2014/0025039 A1* | 1/2014 | Rajendran | A61M 19/00 |
| | | | 604/512 |
| 2016/0106954 A1 | 4/2016 | Hebbard | |
| 2020/0038054 A1* | 2/2020 | Yim | A61B 10/0233 |
| 2020/0121357 A1 | 4/2020 | Gomez et al. | |

* cited by examiner

700

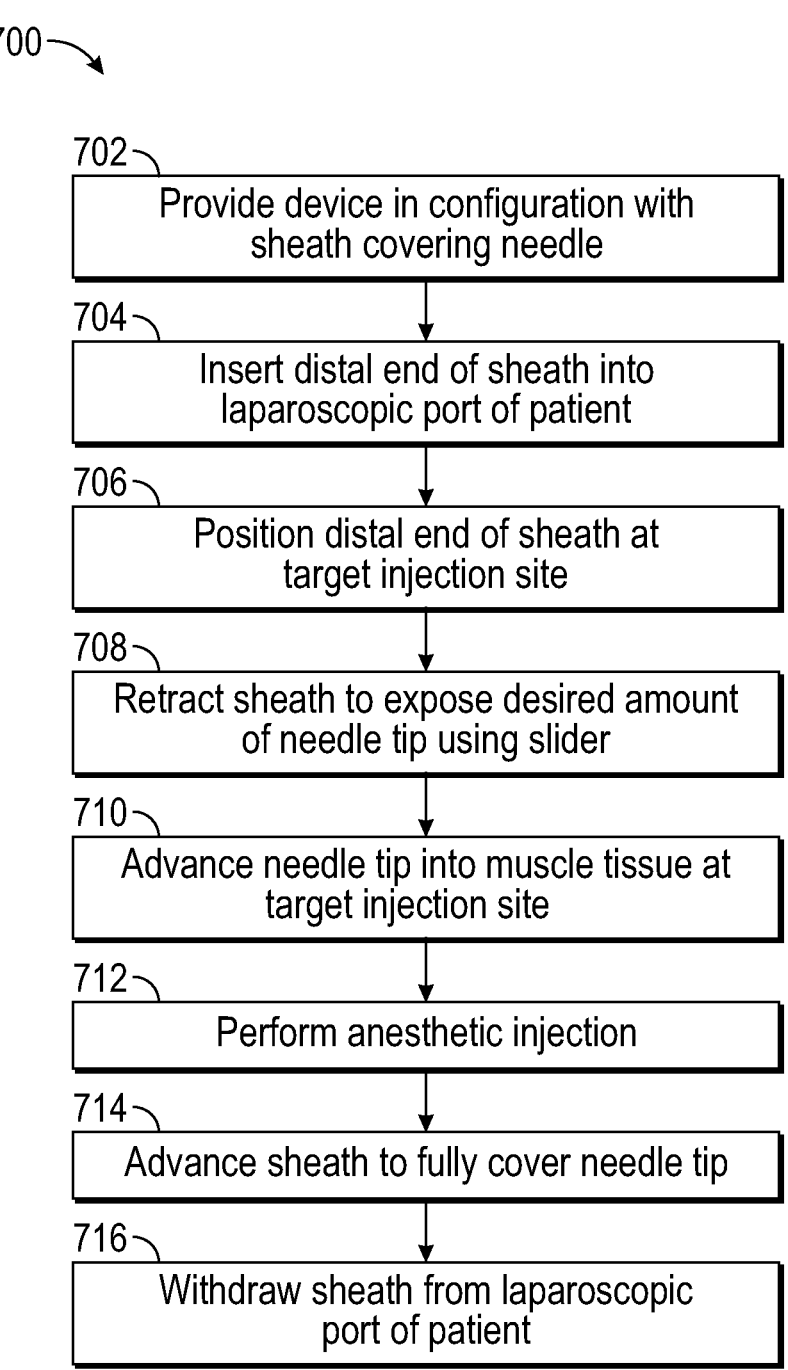

702 — Provide device in configuration with sheath covering needle

704 — Insert distal end of sheath into laparoscopic port of patient

706 — Position distal end of sheath at target injection site

708 — Retract sheath to expose desired amount of needle tip using slider

710 — Advance needle tip into muscle tissue at target injection site

712 — Perform anesthetic injection

714 — Advance sheath to fully cover needle tip

716 — Withdraw sheath from laparoscopic port of patient

FIG. 7

TAP BLOCK INJECTION DEVICE

CROSS-REFERENCE TO RELATED APPLICATION

The present patent application claims priority to U.S. Provisional Patent Application Ser. No. 63/208,293, filed on Jun. 8, 2021, the entire disclosure of which is hereby incorporated herein by reference.

FIELD OF THE INVENTION

The present disclosure relates generally to the field of medical injection devices and, more particularly, to a device for injecting anesthetic into a patient during a laparoscopic surgical procedure, where the device includes a sheath which covers a needle while the device is maneuvered, and the sheath is retractable to expose the needle for the injection.

BACKGROUND

A transversus abdominis plane (TAP) block is a procedure to anesthetize the nerves that provide sensation and muscle function to the abdominal wall and skin of a surgical patient. For a TAP block, an anesthetic injection is administered in the area between the internal oblique and transversus abdominis muscles in the stomach wall. A TAP block reduces the use of post-surgical opioids and their related side effects. A TAP block provides more effective post-surgical pain relief (analgesia) for a longer time period than general anesthesia alone.

A TAP block may be used in open surgical procedures or in laparoscopic procedures. In open surgical procedures, the anesthetic can be administered directly by the surgeon (or other qualified personnel in the operating room) with a syringe/needle in the open body cavity where both access and visibility are good. In laparoscopic procedures, however, access is limited to the small laparoscopic incision(s) or ports, and there is no direct visibility of the surgical field or the needle used for anesthetic injection. With existing injection needles, the limited visibility and maneuverability inherent in laparoscopic procedures increases the risk that the needle will inadvertently puncture an organ or tissue other than the intended transversus abdominis muscle.

In light of the circumstances described above, there is a need for an improved TAP block injection device for use in laparoscopic procedures.

SUMMARY

The present disclosure describes an injection device for performing a transversus abdominis plane (TAP) block anesthetic administration during a laparoscopic surgical procedure. The device includes a handle, a needle fixed to the handle, and a sheath covering the needle. The sheath is slidably retractable via a thumb-operated slider on the handle. In a first position for device insertion and maneuvering, the sheath fully covers the tip of the needle, preventing the needle from puncturing or lacerating any organ or tissue in the patient. In a second position for injection, the sheath is retracted using the slider to expose the tip of the needle, enabling insertion of the needle tip into the appropriate tissue and injection of the anesthetic. The needle and sheath have a length suitable for reaching the desired location internal to the body cavity from outside the patient's body through the laparoscopic incision. A standard threaded luer and tube are fluidly coupled to the needle, where a syringe is attachable to the luer and used to push the anesthetic through the needle and into the tissue.

Additional features of the presently disclosed devices will become apparent from the following description and appended claims, taken in conjunction with the accompanying drawings.

BRIEF DESCRIPTION OF THE DRAWINGS

FIG. 7 is a flowchart diagram of a method for performing a TAP block anesthetic injection during a laparoscopic surgical procedure, according to an embodiment of the present disclosure.

DETAILED DESCRIPTION OF THE EMBODIMENTS

Figure 1:
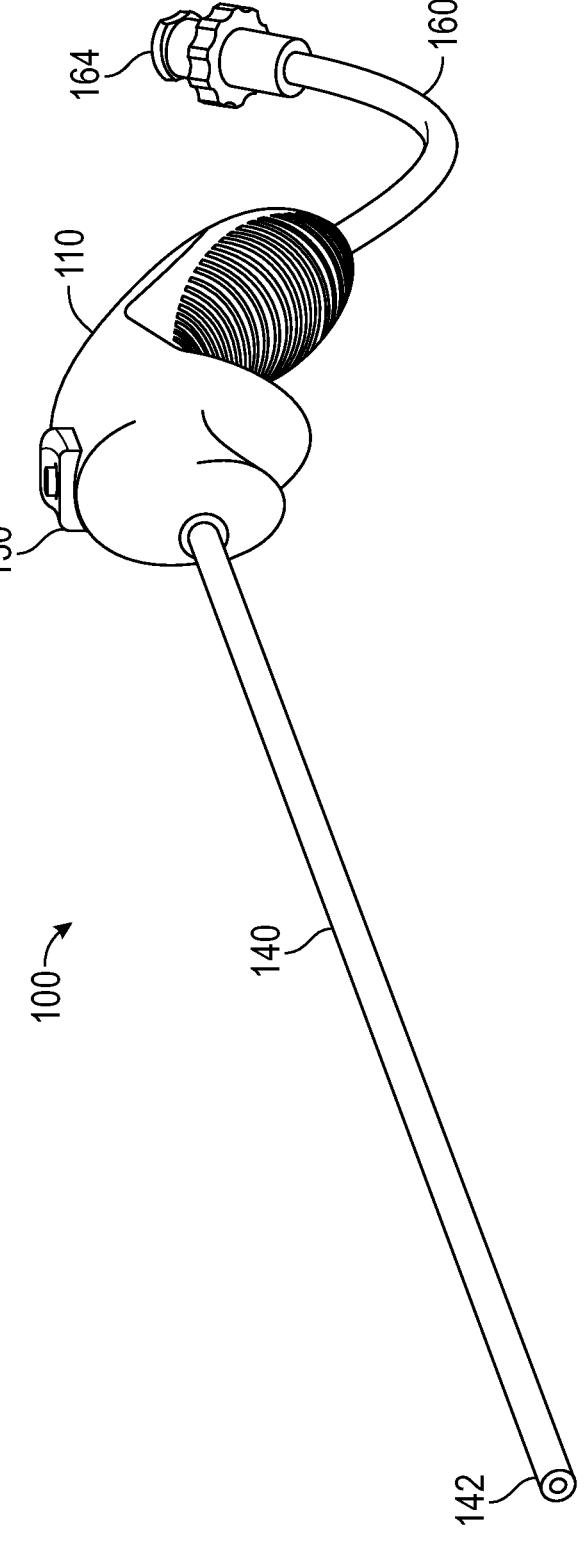
FIG. 1 is a first isometric view illustration of a TAP block injection device, according to an embodiment of the present disclosure.

The following discussion of the embodiments of a TAP block injection device is merely exemplary in nature, and is in no way intended to limit the disclosed devices and techniques or their applications or uses.

A transversus abdominis plane (TAP) block is an anesthetic injection administered to the transversus abdominis muscles in the stomach wall of a patient in order to block pain from surgical incisions. TAP block techniques during abdominal surgeries have expanded in use because the patient recovers more quickly after surgery and associated complications are reduced when a TAP block is used. Furthermore, TAP block techniques decrease reliance on the use of opioids, which can be highly addictive and have been linked to premature deaths. Opioid addiction is a major societal problem and, consequently, wide scale efforts are targeted to reduce reliance on these drugs. Despite the increased use and benefits of TAP block techniques, tools used to perform them need improvement. In addition, there is a dearth of TAP block tools that can be used in conjunction with minimally invasive laparoscopic procedures, whereby the same ports can advantageously be used for both laparoscopic surgery and TAP block techniques to decrease the number of total incisions needed.

The present disclosure describes a device used to perform TAP block injections during laparoscopic procedures. The disclosed device is designed to overcome the limitations of existing tools. The disclosed device offers a dramatic improvement over existing bare injection needles which, whether creating their own puncture hole as advanced into the abdomen or passed through a laparoscopic incision, can inadvertently puncture organs or tissue other than the desired injection target muscle.

The presently disclosed device is designed to be inserted through the laparoscopic incision/port with the needle safely covered by a sheath to prevent puncture of any organ or tissue. The device is advanced into the body cavity and maneuvered into a position where the needle tip, still covered by the sheath, is in the body cavity and pointed outward toward the exterior of the body. When the device is properly positioned in the abdominal cavity, the sheath is retracted and the needle tip is exposed for muscular injection. This design enables the operator, when piercing tissue with the needle, to advance the needle tip from within the body outwardly through tissue, towards the exterior of the body, in a controlled and precise manner to position the needle tip accurately to administer a medicinal substance. The device is designed to puncture through tissue, such as a muscle layer, while providing tactile feedback to the operator during needle insertion.

Throughout the present disclosure, the term "operator" will be used to describe the person who is operating the disclosed TAP block injection device. It is to be understood that the operator may be a surgeon, an anesthesiologist, or any other qualified person who is in the operating room.

The device can be inserted through the same laparoscopic port created in a body to pass devices into and out of that body to access surgical sites, such as a diseased organ, without having to make large abdominal incisions. Used in this manner, the device of the present disclosure enables advancement of the needle through tissue layers, such as muscle, to administer anesthetic agents between muscle layers or to other targeted areas within the body. Importantly, features of this device enable tactile feedback to the operator that signals when the needle tip "pops" through tissue, thus helping to enable an operator to position the needle tip in the fascial layers between muscle tissue, for example. In addition, the direction of insertion of the needle is from within a body towards the outside of that body, which offers a safety advantage over current TAP block techniques that insert the needle from outside the body to within a body, which can lead to unwanted organ perforation or damage by the needle.

The device of the present disclosure includes a slider-type control mechanism on the handle to control and lock the position of the sheath relative to the needle tip. The device also includes a magnetic positioning feature which provides a detent-type tactile feel indicating the position of the slider and thus the position of the sheath relative to the needle tip. The device of the present disclosure can be used in conjunction with imaging equipment that can include ultrasound or fluoroscopic systems to provide visualization within a body to further guide precise needle tip placement.

Figure 2:
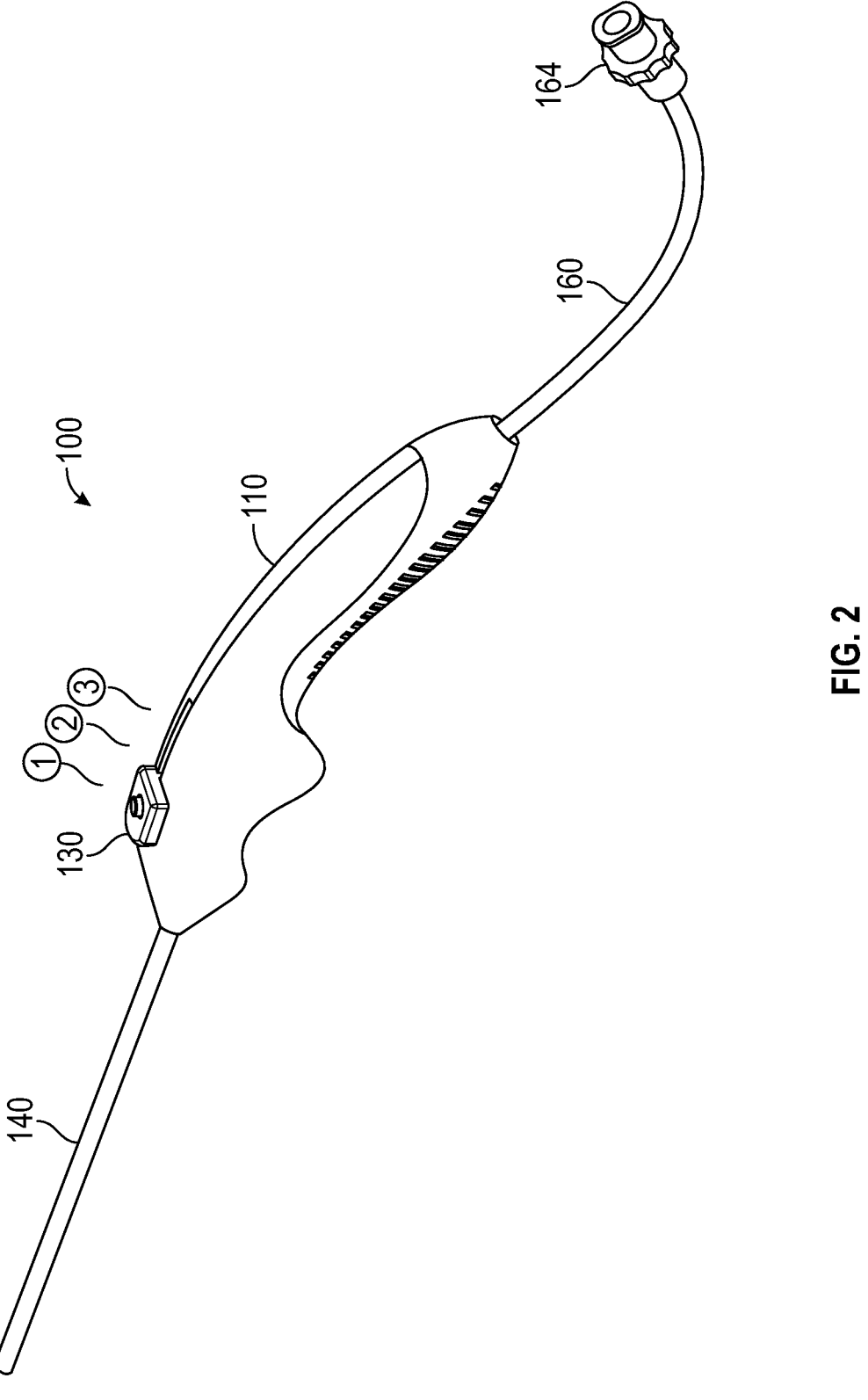
FIG. 2 is a second isometric view illustration of the TAP block injection device, according to an embodiment of the present disclosure.

FIG. 1 is a first isometric view illustration of a TAP block injection device 100, according to an embodiment of the present disclosure. FIG. 2 is a second isometric view illustration of the TAP block injection device 100, according to an embodiment of the present disclosure. The device 100 is comprised of a handle 110, a slider 130 slidably disposed on the handle 110, a sheath 140 and a hypodermic needle 150 (inside the sheath 140 and not visible in FIGS. 1 and 2). The needle 150 is fixedly attached to the handle 110, and an injection port tube 160 is in fluid communication with the needle 150, such that a reservoir such as a syringe (not shown) can be attached to a luer 164 and used to push a liquid such as anesthetic through the tube 160 and the needle 150.

The sheath 140 is coupled to the slider 130. The slider 130 can slide along the top of the handle 110 for a limited travel distance, and has features for locking into different positions. In a preferred embodiment shown in the figures, the slider 130 is lockable in three different positions. When the slider 130 is advanced to the fully-forward position as in FIGS. 1 and 2 (indicated at ① in FIG. 2), the sheath 140 fully covers the tip of the needle 150. In this "safe" position, there is no risk of the needle 150 inadvertently puncturing or perforating any body tissue while the device 100 is being maneuvered into position in the body, because the needle tip is not exposed. When the slider 130 is moved back on the handle 110 to a second position (②) or a third position (③), the sheath 140 is retracted to expose the tip of the needle 150 by a corresponding amount. By way of non-limiting example, at the slider's second position (②) the exposed portion of the needle tip may be 0.75 cm, and at the slider's third position (③) the exposed portion of the needle tip may be 1.5 cm. The different lengths of exposed needle tip allow the operator control over the amount of needle penetration into the target muscle.

The locking feature of the slider 130 (discussed later) ensures that the sheath 140 stays in the operator's desired position relative to the needle 150. In addition, a magnetic positioning feature is included in the slider 130 and the handle 110. The magnetic positioning feature (also discussed later) provides tactile feedback to the operator as to the position of the slider 130 relative to the handle 110, and thus the position of the sheath 140 relative to the tip of the needle 150, so that the operator can concentrate on the position of the needle tip and does not have to look at the slider/handle position.

The device 100 is designed and sized to allow a distal end 142 of the sheath 140 to be advanced into the body cavity through a laparoscopic port, and positioned on an inside fascia of a target muscle pointing in an outwardly direction relative to the patient's body, with the needle 150 fully covered during this insertion and maneuvering. The sheath 140 is then retracted by sliding the slider 130 to the second or third position, the needle 150 is advanced into the muscle by pushing the handle 110 in that direction, and the injection is then administered. In one non-limiting example, the device 100 (excluding the tube 160) has an overall length of about 16 inches, of which 12 inches is the length of the sheath 140 and the needle 150, and 4 inches is the length of the handle 110. Larger or smaller dimensions may be used as suitable for particular TAP block injections.

Figures 3A, 3B, 3C:
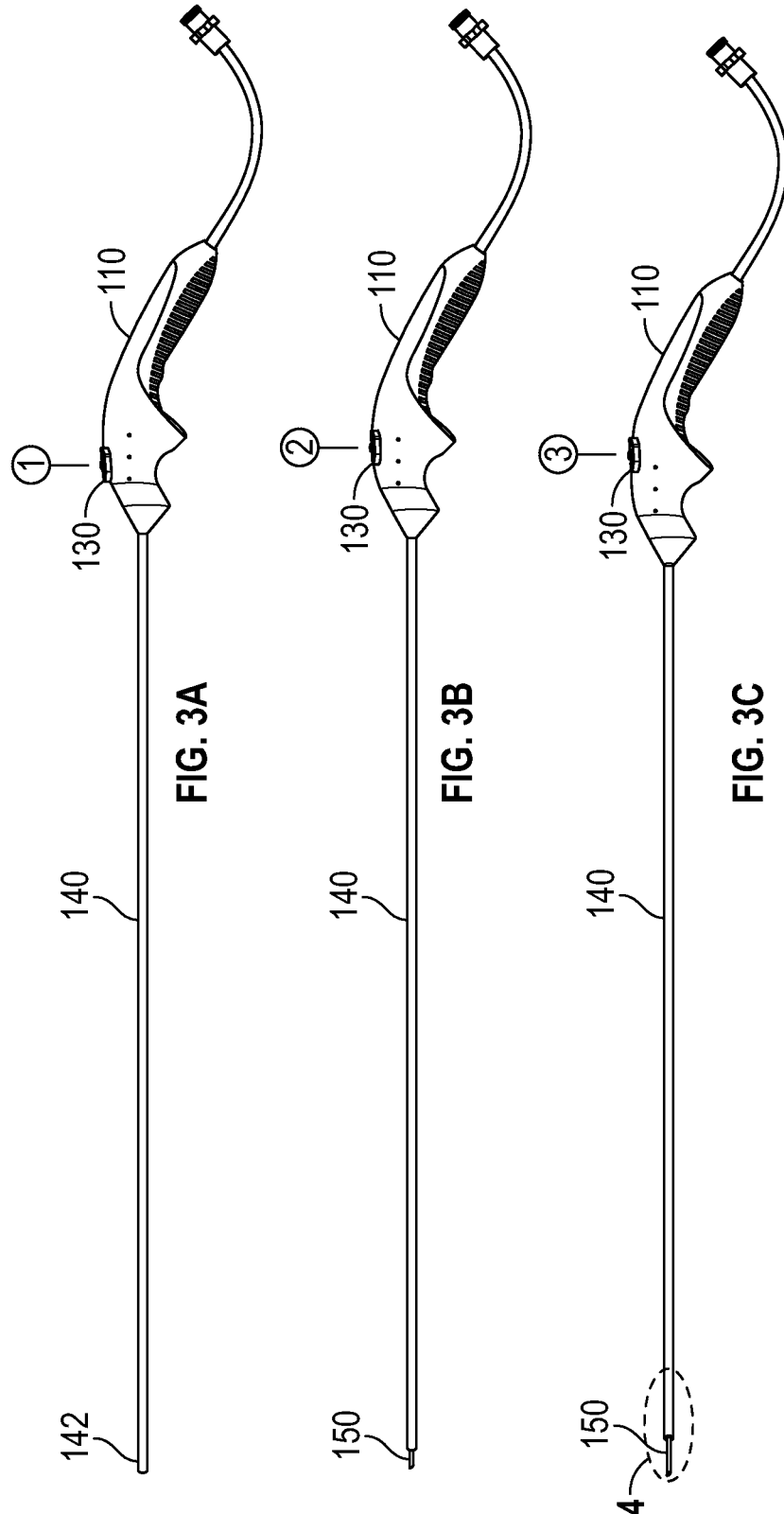
FIGS. 3A/3B/3C are side view illustrations of the TAP block injection device in three different positional configurations, where a needle is fully covered by a sheath or the needle tip is exposed, according to an embodiment of the present disclosure.

FIGS. 3A/3B/3C are side view illustrations of the TAP block injection device 100 in three different positional configurations, where the needle 150 is fully covered by the sheath 140 or the needle tip is exposed, according to an embodiment of the present disclosure. In FIG. 3A, the device 100 is in the same configuration as shown in FIGS. 1 and 2—that is, with the slider 130 advanced to the fully-forward position (①), and the distal end 142 of the sheath 140 fully covering the tip of the needle 150. This is the configuration that is used for insertion of the device 100 into the patient's body through the laparoscopic port and positioning of the device 100 before the injection.

In FIG. 3B, the device 100 is in a configuration with the slider 130 in the middle position (②), and the sheath 140 partially retracted to expose the tip of the needle 150 (by 0.75 cm in one embodiment). This is a configuration that can be used for advancing/penetrating the tip of the needle 150 into the target muscle tissue and injecting the anesthetic. In particular, this configuration would be used when only a limited penetration (0.75 cm) of the needle 150 into the target muscle tissue is desired. In FIG. 3C, the device 100 is in a configuration with the slider 130 in the fully-aft position (③), and the sheath 140 retracted to expose more of the tip of the needle 150 (1.5 cm in one embodiment). This is also a configuration that can be used for advancing/penetrating the tip of the needle 150 into the target muscle tissue and injecting the anesthetic. In particular, this configuration would be used when a greater penetration (1.5 cm) of the needle 150 into the target muscle tissue is desired.

Figure 4:
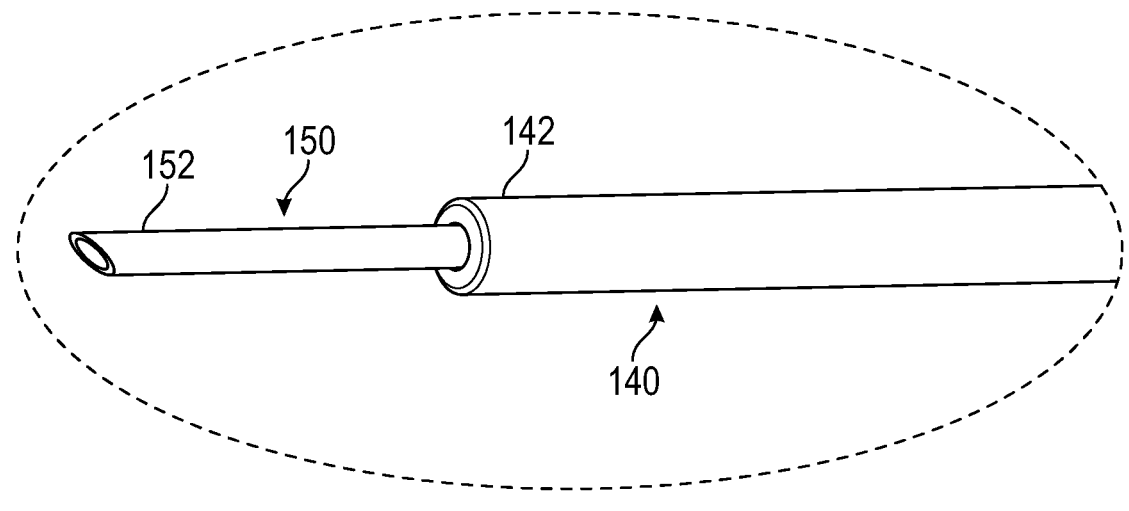
FIG. 4 is a close-up illustration of the TAP block injection device in the configuration of FIG. 3C, where the needle tip is exposed, according to an embodiment of the present disclosure.

FIG. 4 is a close-up illustration of the TAP block injection device 100 in the configuration of FIG. 3C, where the needle tip is exposed, according to an embodiment of the present disclosure. The distal end 142 of the sheath 140 is visible in FIG. 4. The opposite end of the sheath 140, the proximal end, is attached to the slider 130 as discussed above and shown in later figures. The sheath 140 has been retracted from the needle tip by moving the slider 130 to the third (fully-aft) position. A distal end 152 of the needle 150, also referred to as the needle tip, is also visible in FIG. 4. The opposite end of the needle 150, the proximal end, is fixedly mounted inside the handle 110, as mentioned earlier and shown in later figures.

The needle tip is sharpened to an angle that preserves tactile feedback to the operator as it penetrates tissue. The preferred angle of the sharpened needle tip is 45 degrees. A 45-degree angle of the needle tip provides an optimal balance of force required to penetrate tissue while preserving tactile feedback of the needle tip during use. When penetrating a fascial layer of muscle tissue, the optimized needle angle exhibits a "pop" sensation to the operator as he or she advances the needle 150 through the tissue layer. The "pop" sensation is an indicator that the needle tip has exited one layer of tissue and that the needle tip may be in the interstitial space between layers of tissue, such as muscle.

Other tip angles also provide acceptable performance. The needle tip angle can range from around 30 degrees to around 60 degrees, with 45 degrees being the preferred sharpened tip angle. The needle 150 can be made from any material commonly used for hypodermic needles, such as medical grade 304 or 316 stainless steel. Other grades of stainless steel used in the medical device industry for hypodermic needles can also be used. It is also contemplated that other materials like a shape memory alloy, such as nitinol may also be used for the needle 150. The inner and outer diameter, ID and OD respectively, of the hypotube used to make the needle 150 can be of any size commonly utilized to administer anesthetic agents. For example, a 27-gauge needle tube with an ID of 0.21 mm and OD of 0.413 mm with a nominal needle wall thickness of 0.102 mm is suitable in this application. Alternatively, other hypotube sizes, such as a 25 or 30 gauge can be used. Still other hypotube sizes can also be used.

In a preferred embodiment, the needle 150 is straight as shown in the figures. In other embodiments, the needle 150 may be curved in any amount and any direction to suit a particular application. The shape memory alloy mentioned above may be used to increase or decrease needle curvature or change the shape of curvature (by heating the needle 150) during the TAP block procedure. For example, a needle shape with little or no curvature may be best suited for accessing a first TAP block injection site, and a needle shape with significant curvature may be best suited for assessing a second TAP block injection site during the same laparoscopic surgical procedure.

The device 100 of the present disclosure can be used in conjunction with imaging equipment that can include ultrasound or fluoroscopic systems to provide visualization of the needle 150 within a patient's body to further guide precise needle tip placement.

The operation of the sheath 140 has been discussed above—where the sheath 140 fully covers the needle tip on one configuration, the sheath 140 is connected to the slider 130, and movement of the slider 130 allows the sheath 140 to be retracted from the needle tip. In one embodiment, the working length of the sheath 140 can be 12 inches (30 cm) and its diameter can be 0.125 inches (3.2 cm). Other sheath working lengths and diameters can be used. The sheath working length is the length of the sheath 140 from the distal end of the handle 110 (where the sheath 140 connects to the slider 130) to the distal end 142 of the sheath 140. This sheath working length is available to insert into a patient's body. The sheath 140 can be made from a variety of materials that include flexible polymers to inflexible metallic tubing. Examples of suitable polymers include biocompatible polyurethane, nylon, polycarbonate, polyether block amide (PEBA), polyethylene, and other polymer materials commonly used in medical devices used within the body. The sheath 140 can also be made of a variety of medical grade stainless steel or a shape memory alloy such as nitinol, in designs compatible with the shape and material of the needle 150. The inner diameter of the sheath 140 is larger than the outer diameter of the needle 150, thus enabling free movement of the needle 150 within the sheath 140.

Figure 5:
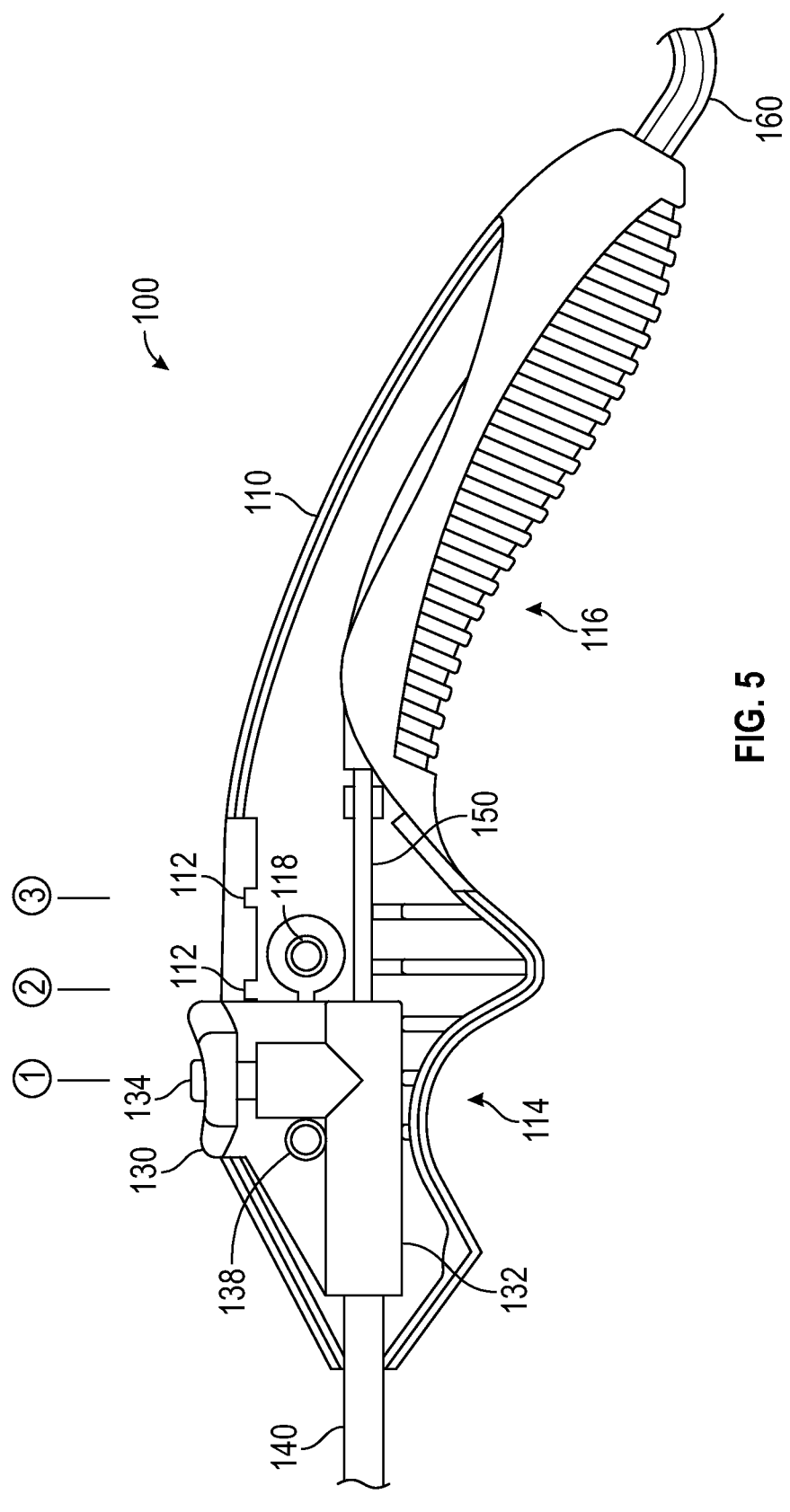
FIG. 5 is a partially cut-away illustration of the handle of the TAP block injection device, showing details of a slider for positioning the sheath, according to an embodiment of the present disclosure.

FIG. 5 is a partially cut-away illustration of the handle 110 of the TAP block injection device 100, showing operational details of the slider 130 for positioning the sheath 140, according to an embodiment of the present disclosure. The slider 130 is designed to be thumb-operated by the operator. As discussed previously, the operator manually advances or retracts the position of the slider 130 to vary the exposed length of the needle 150. Throughout the present disclosure, slider positions described as "advance(d)" and "fully-forward" correspond to the first position (①) of the slider 130 relative to the handle 110, as illustrated in FIGS. 1, 2, 3A and 5, where the needle tip is fully covered by the sheath 140. Slider positions described as "partially retracted" correspond to the second position (②) of the slider 130 relative to the handle 110, where the slider 130 is in this position in FIG. 3B. Similarly, slider positions described as "fully retracted" and "fully-aft" correspond to the third position (③) of the slider 130 relative to the handle 110, where the slider 130 is in this position in FIG. 3C, and the position is designated by the ③ in other figures. The slider 130 can be retracted from the fully-forward position (where no portion of the needle 150 is exposed) to a partially-retracted or fully-retracted position where the needle tip is exposed. The slider 130 can be advanced from a partially-retracted or fully-retracted position to the fully-forward position to completely cover the needle tip with the sheath 140.

The slider 130 is attached to the sheath 140 at a coupler 132, so the slider 130 and the sheath 140 move together. The coupler 132 and the slider 130 operate as a single part, and can be molded as a single-piece unit, or molded separately and joined together. The sheath 140 is pressed and/or bonded into an aperture in the coupler 132, so that the sheath 140 is permanently fixed to the coupler 132 and thus the slider 130. The slider 130 slides along the handle 110, thus controlling the position of the sheath 140 with respect to the needle 150, where the needle 150 is immovably affixed within the housing of the handle 110 as shown in FIG. 5. The proximal end of the needle 150 is in fluid communication with the interior of the injection port tube 160, so that anesthetic from a reservoir (e.g., syringe) coupled to the luer 164 can be pushed through the needle 150.

Figure 6:
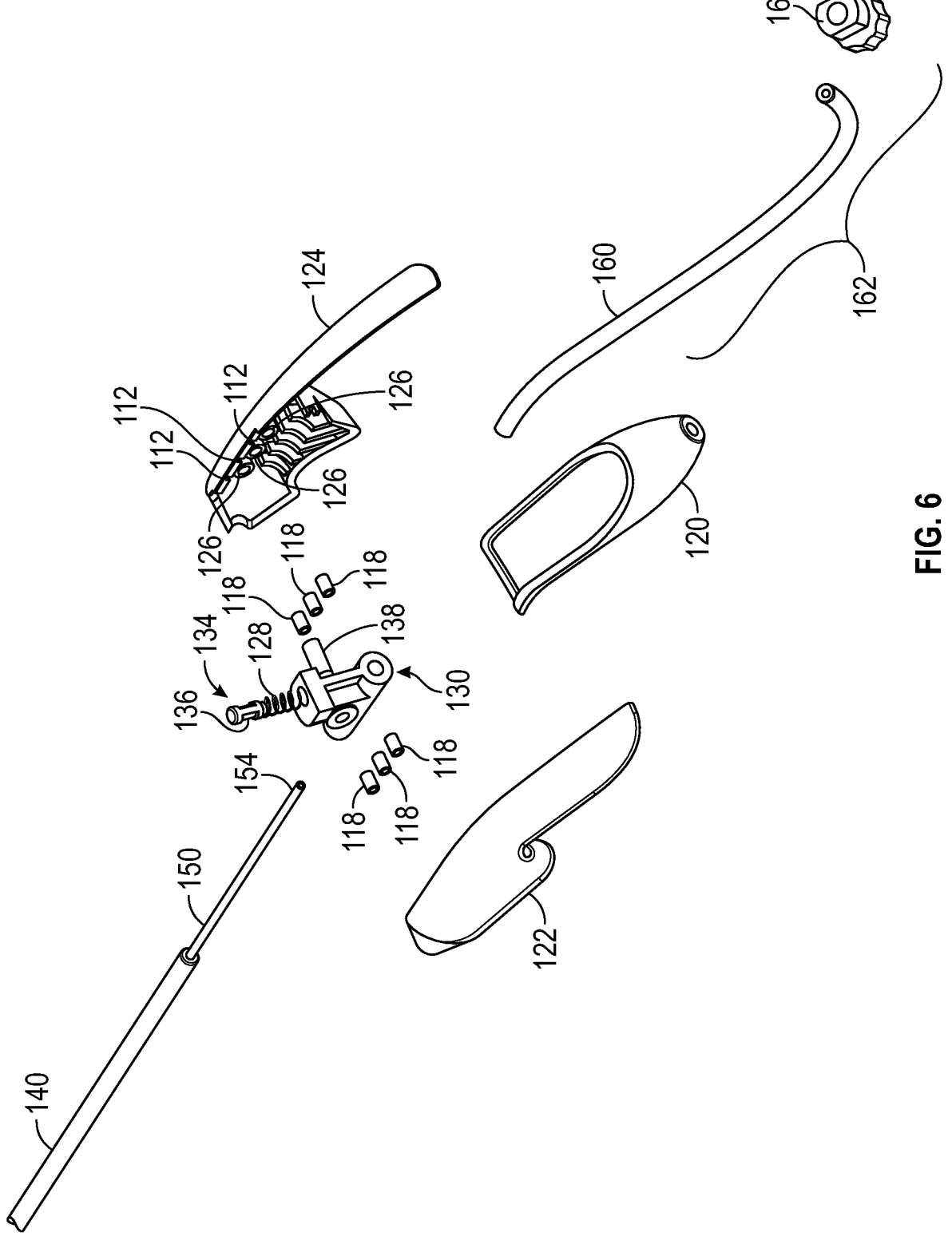
FIG. 6 is an exploded-view illustration of the TAP block injection device, according to embodiments of the present disclosure.

The slider 130 has a slider lock button 134 to immobilize the position of the slider 130 relative to the handle 110, and thus lock the position of the sheath 140 relative to the needle 150. The slider lock button 134 is spring-loaded ("upward" in FIG. 5) and has a shape feature designed to lock into notches 112 on an upper interior surface of the handle 110. These features are shown in FIG. 6 and discussed further below. Depressing the slider lock button 134 (by the thumb of the operator) releases the slider 130 to enable the slider 130 to move back and forth along a track of the handle 110. When the slider lock button 134 is released, the spring-loading pushes the button 134 upward to engage one of the notches 112 and lock the slider 130 in position with respect to the handle 110. In the preferred embodiment, there are three of the notches 112. The locations of the notches 112 correspond to the positions (①, ② and ③) of the slider 130, where the aft-most two of the notches 112 are visible in FIG. 5. When the slider lock button 134 is locked into position in one of the notches 112, the slider 130 is immobilized relative to the handle 110, and the sheath 140 is thus fixed in position relative to the needle 150.

In addition to the slider position locking feature discussed above, the device 100 includes a magnetic positioning feature in the slider 130 and the handle 110. The magnetic positioning feature provides tactile feedback to the operator as to the position of the slider 130 relative to the handle 110, while the slider lock button 134 is depressed, so that the operator can concentrate on the position of the needle tip and does not have to look at the handle 110 in order to determine the position of the slider 130. In a preferred embodiment, the magnetic positioning feature includes a magnet rod 138 fitted transversely into the slider 130, and pairs of steel pins 118 fitted into the left and right sides of the handle 110. A left/right pair of the steel pins 118 is provided for each of the lock positions (①, ② and ③) of the slider 130; thus, there are three pairs of the pins 118 in the preferred embodiment. One of the steel pins 118 is visible in FIG. 5. Further details are shown in FIG. 6.

The magnet rod 138 aligns with one of the pairs of steel pins 118 when the slider lock button 134 is aligned with one of the notches 112, thus providing a detent-type feel to the operator indicating that the slider 130 is in one of the three positions. In this way, when the slider lock button 134 is released with the slider 130 at one of the three notch positions, the slider lock button 134 snaps up into one of the notches 112 and the slider 130 is locked in position.

The needle 150 inside the sheath 140 serves to guide the coupler 132 and the slider 130 in controlled linear fore/aft motion, as seen in FIG. 5. The travel distance of the slider 130 dictates the length of travel of the sheath 140. There is a 1:1 correlation between the length of the movement of the slider 130 and the sheath 140. The total travel distance is designed to be 1.5 cm in the preferred embodiment. However, other total travel distances are contemplated. Similarly, the device 100 of the present disclosure can be designed to offer a variety of amounts of exposed needle tip. In the embodiment shown in the figures of the present disclosure, the operator can advance the sheath 140 to cover the needle 150 completely, or retract the sheath 140 to expose 0.75 cm of the needle tip, or expose 1.5 cm of the needle tip, depending on the position of the slider 130. Other slider/sheath position combinations are readily envisioned and possible—such as a two-position design (needle covered vs. exposed), a four-position design, etc. In other embodiments, the distances between the slider lock positions need not all be the same, and the maximum possible amount of exposed needle tip may be more or less than the 1.5 cm of the embodiment discussed above.

The handle 110 has a shape designed to fit the operator's hand (either hand), where the index finger is wrapped around the handle 110 and positioned in a recess 114 on the bottom of the handle 110 near the front, and the three other fingers are wrapped around the handle 110 and positioned on the bottom of the handle 110 at the middle and rear as indicated at 116. Features are provided to ensure a positive grip on the handle 110, such as grooves or a knurled surface, particularly in the middle and rear as indicated at 116. The operator's thumb is positioned on the top front of the handle 110 to operate the slider 130.

FIG. 6 is an exploded-view illustration of the TAP block injection device 100, according to embodiments of the present disclosure. In one design embodiment, the handle 110 is constructed of three pieces—including a handle grip 120 which makes up the lower portion of the handle 110, and a handle left half 122 and a handle right half 124 which make up the left and right sides and upper portion of the handle 110, respectively. Other handle construction embodiments are also possible. The sheath 140 and the needle 150 are shown as described previously—where the needle 150 is positioned inside the sheath 140. A proximal end 154 of the needle 150 is fitted into the injection port tube 160 and the needle 150 and the tube 160 are fixed to the handle 110, such as by snapping into clips molded into one or both of the handle half parts 122/124 and being held in place between the handle left half 122 and the handle right half 124.

The sheath 140 is fixed to the slider 130 at the coupler 132 (labelled on FIG. 5). Thus, fore/aft movement of the slider 130 relative to the handle 110 causes the sheath 140 to extend or retract relative to the needle 150, as described in detail above.

The slider lock button 134 fits into a hole in the top of the slider 130. A compression spring 128 is installed in the hole before the slider lock button 134, where the spring 128 provides an upward bias force on the bottom of the slider lock button 134. A shoulder 136 is a shape feature located on each side of the slider lock button 134. The shoulder 136 fits into the notches 112 in the handle 110. The three notches 112 are visible in the handle right half 124 in FIG. 6. When the slider lock button 134 is depressed, compressing the spring 128, the shoulder 136 is displaced downward out of whichever of the notches 112 it was in, and the slider 130 is free to move fore and aft. When the slider lock button 134 is released with the shoulder 136 aligned with one of the three notch positions, the slider lock button 134 snaps up into one of the notches 112 and the slider 130 is locked in position.

Details of the components of the magnetic positioning feature are also clearly visible in FIG. 6. A plurality of the steel pins 118 are fitted into holes 126 in the handle left half 122 and the handle right half 124. Specifically, a pair of the steel pins 118 (one each on left and right sides) is provided for each locking position of the slider 130 relative to the handle 110. Three of the holes 126 are visible in the handle right half 124; three of the holes 126 are provided at corresponding (directly opposite) locations in the handle left half 122. The magnet rod 138 is fitted transversely into the slider 130. When the slider 130 is moved fore/aft, the magnet rod 138 is attracted to align with one of the pairs of the steel pins 118, thus providing a strong tactile feel to the operator as to the position of the slider 130 relative to the handle 110. The fore/aft positions of the magnet rod 138 relative to the shoulder 136 in the slider 130, and the holes

126 relative to the notches 112 in the left and right handle halves 122/124, are designed such that when the magnet rod 138 is aligned with one of the pairs of pins 118, the shoulder 136 is aligned with a corresponding notch 112. In this way, when the operator feels the detent-type click of magnetic alignment, he/she knows which position (①, ② or ③) the slider 130 is in, and knows that the slider 130 will lock into that position when the slider lock button 134 is released. This tactile slider position feedback is important in that it allows the operator to concentrate on the needle tip place- ment displayed on an imaging system during the surgical procedure, and not have to look at the handle 110 in order to determine slider position.

An injection port assembly 162 is comprised of the tube 160 which is a flexible polymer tube, and the luer 164 which is a standard threaded luer. This assembly 162, in turn, is attached to the needle 150, with the needle 150 pressed into the tube 160. The needle 150, the tube 160 and luer 164 are fused together to ensure that there are no leaks at each of the joints between the different components. The method of fusing or bonding the needle 150 to the tube 160 can include a self-bonding friction fit, adhesive bonding or heat boding to attach the tube 160 directly onto the needle 150. Similarly, the tube 160 is bonded to the luer 164 using either adhesive or heat bonding so that no leaks occur between the compo- nents. Examples of suitable polymers for the flexible poly- mer tubing in the injection port assembly 162 include biocompatible polyurethane, nylon, polycarbonate, PEBA, polyethylene and other polymer materials commonly used in medical devices. The standard threaded luer 164 is an off the shelf component made from polycarbonate, or other similar materials, and is widely available to medical device manu- facturers from component suppliers.

The sheath 140 of the device 100 is designed to fit through a 5 mm laparoscopic port. An adaptor could be fit to allow the device 100 to be used with any size port. The device 100 can also be used with a da Vinci surgical robot through a port adapter. Additionally, the device 100 of the present disclo- sure could be adapted to fit into a da Vinci arm and, therefore, be manipulated and positioned by the da Vinci surgical robot.

FIG. 7 is a flowchart diagram 700 of a method for performing a TAP block anesthetic injection during a lapa- roscopic surgical procedure, according to an embodiment of the present disclosure. At box 702, the device 100 is pro- vided in a first configuration where the sheath 140 is extended and locked to fully cover a needle tip of a hypo- dermic needle 150. At box 704, the distal end 142 of the sheath 140 is inserted into a laparoscopic port of a patient. At box 706, the distal end 142 of the sheath 140 is directed towards the abdominal wall and positioned at a target injection site inside the patient.

At box 708, the sheath 140 is retracted to expose a desired amount of the needle tip, using the slider 130 on a handle 110 of the injection device 100. The operator depresses the slider lock button 134 while simultaneously pulling back on the slider 130 to expose the tip of the needle 150. The sheath 140 is locked in a position which exposes the desired amount of the tip of the needle 150. Once the tip of the needle 150 is exposed, at box 710, the needle tip is advanced into the desired plane of the transverse abdominal muscle tissue at the target injection site, where the operator feels the distinc- tive "pop" when entering fascial tissue.

At box 712, the anesthetic injection is performed by expelling anesthetic from a syringe connected to the luer 164. The surgeon can either perform the injection of local anesthetic himself/herself, or can have an assistant (other operator) perform the injection as the device 100 of the present disclosure design allows for either method, depend- ing on surgeon preference. The injection is performed by pressing a plunger on a syringe attached to the luer 164, in a known manner. During the injection, the operator will notice a bulge of the transverse abdominal muscle as the pressure from the local anesthetic in the fascial plane pushes the thin muscle into the abdominal cavity, resulting in the appearance of said bulge, which is a sign of proper needle positioning and infusion of the anesthetic agent.

At this point, if additional anesthetic needs to be injected at a greater depth in the muscle, the operator can retract the sheath 140 to expose a greater amount of the tip of the needle 150, then insert the needle 150 the additional distance into the muscle, and again perform an injection. After the desired amount of local anesthetic has been administered, at box 714 the operator presses the slider lock button 134 and moves the slider 130 forward to fully cover the needle 150 with the sheath 140, while withdrawing the tip of the needle 150 from the muscle.

At box 716, the sheath 140 is withdrawn from the laparoscopic port of the patient. The operator then performs the same technique on the contralateral side. All insertion, maneuvering and withdrawal of the device 100 in and from the patient occurs with the sheath 140 locked in the fully- forward position and fully covering the needle 150, thus ensuring that no inadvertent puncture, perforation or lacera- tion of tissue or organs occur.

The device 100 and the method of the flowchart 700 could also be used to perform injections at other sites besides the transversus abdominis muscles, in any application which benefits from a device which can be inserted into a laparo- scopic port, safely maneuvered inside the body with the needle tip covered, then re-configured to expose the needle tip and perform the injection.

The presently disclosed TAP block injection device 100 offers many advantages over existing tools. The device 100 can be advanced through the same laparoscopic port created in a body to pass devices into and out of that body to access surgical sites, such as a diseased organ, without having to make large abdominal incisions. Used in this manner, the device of the present disclosure enables advancement of the needle through tissue layers, such as muscle, to administer anesthetic agents between muscle layers or to other targeted areas within the body. Importantly, features of this device enable tactile feedback to the operator that signals when the needle tip "pops" through tissue, thus helping to enable an operator to position the needle tip in the fascial layers between muscle tissue, for example. In addition, the direc- tion of insertion of the needle is from within the body towards the outside of that body, which offers a safety advantage over current TAP block techniques that insert the needle from outside the body to within the body, which can lead to unwanted organ perforation or damage by the needle. The sheath-covered needle provides a tremendous safety advantage over existing tools, and the convenient means of retracting the sheath for injection provides the necessary device control, including tactile feedback of configuration, while allowing the operator to concentrate on device posi- tioning rather than operation.

While a number of exemplary aspects and embodiments for a TAP block injection device have been discussed above, those of skill in the art will recognize modifications, per- mutations, additions and sub-combinations thereof. It is therefore intended that the following appended claims and claims hereafter introduced are interpreted to include all such modifications, permutations, additions and sub-combinations as are within their true spirit and scope.

What is claimed is:

1. An injection device comprising:
a handle;
a control mechanism on the handle;
a hypodermic needle having a proximal end fixed in the handle and a needle tip at a distal end outside the handle;
a sheath concentrically disposed around the needle, said sheath being coupled to the control mechanism on the handle, where the sheath is extendable to fully cover the needle tip and retractable to expose a portion of the needle tip via movement of the control mechanism; and
an injection port assembly including a tube having a distal end fluidly coupled to the needle and a proximal end with a threaded luer attached;
wherein the control mechanism is a thumb-operated slider slidably disposed along a top of the handle, and wherein the slider has a slider lock button biased toward notches in an interior surface of the top of the handle, wherein the slider lock button engages one of the notches to lock the slider and the sheath in position relative to the handle, and wherein the slider lock button is depressed to release the slider and extend or retract the sheath relative to the needle.

2. The device according to claim 1, wherein the slider includes a magnet rod positioned transversely through the slider and the magnet rod is attracted into alignment with one of three opposing pairs of steel pins fitted into the handle, where each alignment of the magnet rod with one of the pairs of steel pins corresponds with slider lock button alignment with one of the notches.

3. The device according to claim 1, wherein the control mechanism is lockable at a first position where the sheath fully covers the needle tip, and at least one other position where the sheath is retracted to expose the needle tip.

4. The device according to claim 1, wherein the portion of the needle tip exposed when the sheath is retracted is in a range from 0.5-2.0 cm.

5. The device according to claim 1, wherein the needle is constructed of stainless steel.

6. The device according to claim 1, wherein the needle is constructed of a shape memory alloy, and where the needle is heatable to change a shape of the needle during a surgical procedure.

7. The device according to claim 1, wherein the needle tip is sharpened to an angle of 45 degrees, +/−15 degrees, relative to a length of the needle.

8. The device according to claim 1, wherein the sheath has an outside diameter of less than 0.4 cm.

9. The device according to claim 1, wherein the sheath is constructed of a polymer, stainless steel or a shape memory alloy.

10. The device according to claim 1, wherein a syringe connected to the threaded luer is operable to push a liquid from the syringe through the tube, into the needle and out the needle tip.

11. A device for performing a transversus abdominis plane (TAP) block anesthetic injection during a laparoscopic surgical procedure, said device comprising:
a handle;
a thumb-operated slider slidably disposed on a top of the handle, said slider having a slider lock button spring-biased toward notches in an interior surface of the top of the handle, where the slider lock button engages one of the notches to lock the slider in one of a plurality of positions relative to the handle and the slider lock button is depressed to unlock and move the slider, and the slider includes a magnet rod positioned transversely through the slider and the magnet rod is attracted into alignment with one of a plurality of opposing pairs of steel pins fitted into the handle, where each alignment of the magnet rod with one of the pairs of steel pins corresponds with slider lock button alignment with one of the notches;
a hypodermic needle having a proximal end fixed inside the handle and a needle tip at a distal end outside the handle;
a sheath concentrically disposed around the needle, said sheath being coupled to the slider on the handle, where the sheath is extendable to fully cover the needle tip and retractable to expose a portion of the needle tip via movement of the slider;
an injection port tube extending from an end of the handle opposite the sheath, said tube having a first end fluidly coupled to the needle inside the handle; and
a threaded luer attached to a second end of the tube, where a syringe connected to the threaded luer is operable to push a liquid anesthetic from the syringe through the tube, into the needle and out the needle tip.

12. The device according to claim 11, wherein the plurality of positions where the slider is lockable relative to the handle include a first position where the sheath fully covers the needle tip, a second position where the sheath is retracted to expose 0.65-0.85 cm of the needle tip, and a third position where the sheath is retracted to expose 1.4-1.6 cm of the needle tip.

13. The device according to claim 11, wherein the sheath has a working length external to the handle in a range of 25-35 cm and an outside diameter in a range of 0.25-0.35 cm.

14. The device according to claim 11, wherein the needle is constructed of stainless steel and the needle tip is sharpened to an angle of 45 degrees, +/−5 degrees, relative to a length of the needle.

15. A method for performing a transversus abdominis plane (TAP) block anesthetic injection during a laparoscopic surgical procedure, said method comprising:
providing an injection device including a handle, a control mechanism on the handle, a hypodermic needle having a needle tip, and a sheath concentrically disposed around the hypodermic needle with said sheath coupled to the control mechanism on the handle, wherein the control mechanism is a thumb-operated slider slidably disposed along a top of the handle, and wherein the slider has a slider lock button biased toward notches in an interior surface of the top of the handle, wherein the slider lock button engages one of the notches to lock the slider and the sheath in position relative to the handle, and wherein the slider lock button is depressed to release the slider and extend or retract the sheath relative to the needle, wherein the injection device is provided in a first configuration where the sheath is extended to fully cover the needle tip of the hypodermic needle;
inserting a distal end of the sheath into a laparoscopic port of a patient;
positioning the distal end of the sheath at a target injection site;
retracting the sheath after depressing the slider lock button to release the slider, to expose a desired length of the needle tip, using the control mechanism on the handle of the injection device;

advancing the needle tip into muscle tissue at the target injection site;

performing the anesthetic injection by expelling anesthetic from a syringe connected to a luer, where the luer is fluidly coupled to a first end of a tube and a second end of the tube is fluidly coupled to the hypodermic needle;

advancing the sheath after depressing the slider lock button to release the slider to fully cover the needle tip using the control mechanism, thereby returning the device to the first configuration; and withdrawing the sheath from the laparoscopic port of the patient.

16. The method according to claim 15, further comprising using imaging equipment, including ultrasound or fluoroscopic systems, during the surgical procedure to provide visualization of the hypodermic needle within a body of the patient.

17. The method according to claim 15, wherein the slider is lockable at a first position where the sheath fully covers the needle tip, and at least one other position where the sheath is retracted to expose a length of the needle tip.

18. The method according to claim 15, further comprising changing a shape of the hypodermic needle by heating the hypodermic needle during the surgical procedure, where the hypodermic needle is constructed of a shape memory alloy.

\* \* \* \* \*